(12) United States Patent
Yuasa

(10) Patent No.: US 9,299,134 B2
(45) Date of Patent: Mar. 29, 2016

(54) OPTICAL TOMOGRAPHIC IMAGING APPARATUS

(75) Inventor: Takashi Yuasa, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 158 days.

(21) Appl. No.: 13/575,730

(22) PCT Filed: Mar. 18, 2011

(86) PCT No.: PCT/JP2011/057505
§ 371 (c)(1),
(2), (4) Date: Jul. 27, 2012

(87) PCT Pub. No.: WO2011/118826
PCT Pub. Date: Sep. 29, 2011

(65) Prior Publication Data
US 2012/0300217 A1   Nov. 29, 2012

(30) Foreign Application Priority Data

Mar. 25, 2010 (JP) ................................. 2010-070029
Mar. 17, 2011 (JP) ................................. 2011-058979

(51) Int. Cl.
*G01B 9/02* (2006.01)
*G06T 7/00* (2006.01)
(Continued)

(52) U.S. Cl.
CPC .............. *G06T 7/0002* (2013.01); *A61B 3/102* (2013.01); *G06T 7/0014* (2013.01); *A61B 5/0066* (2013.01);
(Continued)

(58) Field of Classification Search
CPC ..................... G06T 7/002; G06T 2207/30041; G06T 2207/30168; G06T 2207/20104; G06T 2207/10101; A61B 5/0066; A61B 3/102
See application file for complete search history.

(56) References Cited

U.S. PATENT DOCUMENTS 5,838,365 A  * 11/1998  Sawasaki .............. G06F 17/153
                                                          342/189
8,018,598 B2     9/2011  Cense et al.
(Continued)

FOREIGN PATENT DOCUMENTS

JP    2003-093347 A    4/2003
JP    2009-042197 A    2/2009
KR   10-2007-0062456 A   6/2007

OTHER PUBLICATIONS

Oct. 4, 2012 International Preliminary Report on Patentability in International Patent Appln. No. PCT/JP2011/057505.
(Continued)

*Primary Examiner* — Kara E Geisel
*Assistant Examiner* — Hina F Ayub
(74) *Attorney, Agent, or Firm* — Fitzpatrick, Cella, Harper & Scinto

(57) ABSTRACT

Provided is an optical tomographic imaging apparatus including: a unit for creating a measuring beam and a reference beam from beam of a light source, and generating interference light by combining a return beam resulting from the measuring beam and the reference beam; a unit for detecting the interference light to generate a detection signal; a unit for forming an image of the object based on the detection signal; a unit for designating a specific area in the image; a unit for setting a calculation index and a determination reference range used for determining image quality of the specific area; and a unit for applying calculation processing to a luminance value of the specific area based on the calculation index, determining whether a calculated value obtained as a result of the calculation processing is within the determination reference range, and outputting a detection result.

19 Claims, 4 Drawing Sheets

(51) Int. Cl.
*A61B 3/10* (2006.01)
*A61B 5/00* (2006.01)

(52) U.S. Cl.
CPC ......... *G01B 9/02091* (2013.01); *G01B 2290/70* (2013.01); *G06T 2207/10101* (2013.01); *G06T 2207/20104* (2013.01); *G06T 2207/30041* (2013.01); *G06T 2207/30168* (2013.01)

(56) References Cited

U.S. PATENT DOCUMENTS

| | | | |
|---|---|---|---|
| 2003/0053699 A1* | 3/2003 | Olsson | 382/228 |
| 2004/0242987 A1* | 12/2004 | Liew et al. | 600/407 |
| 2005/0053309 A1* | 3/2005 | Szczuka et al. | 382/284 |
| 2008/0090199 A1* | 4/2008 | Noguchi | A61B 5/0088 433/29 |
| 2008/0240583 A1* | 10/2008 | Jones | 382/232 |
| 2009/0074279 A1* | 3/2009 | Razifar | G06T 5/008 382/131 |
| 2009/0196477 A1 | 8/2009 | Cense et al. | |
| 2010/0049549 A1* | 2/2010 | Nelms | G06Q 10/10 705/3 |
| 2010/0142767 A1* | 6/2010 | Fleming | G06K 9/0061 382/117 |
| 2010/0157311 A1* | 6/2010 | Hayashi et al. | 356/496 |
| 2011/0242487 A1 | 10/2011 | Yuasa et al. | |
| 2012/0051614 A1* | 3/2012 | Olszewski | G06T 7/0002 382/128 |
| 2012/0053904 A1 | 3/2012 | Yuasa et al. | |
| 2012/0176507 A1* | 7/2012 | Quan et al. | 348/222.1 |
| 2013/0223717 A1* | 8/2013 | Reboni et al. | 382/131 |

OTHER PUBLICATIONS

Jun. 14, 2011 International Search Report and Written Opinion in International Patent Appln. No. PCT/JP2011/057505.

Mariane B. Mellem-Kairala, et al., "Improved Contrast of Peripapillary Hyperpigmentation Using Polarization Analysis", Investigative Ophthalmology & Visual Science, vol. 46, No. 3, Mar. 2005, pp. 1099-1106.

Jun. 12, 2015 Chinese Official Action in Chinese Patent Appln. No. 201180015879.1.

* cited by examiner

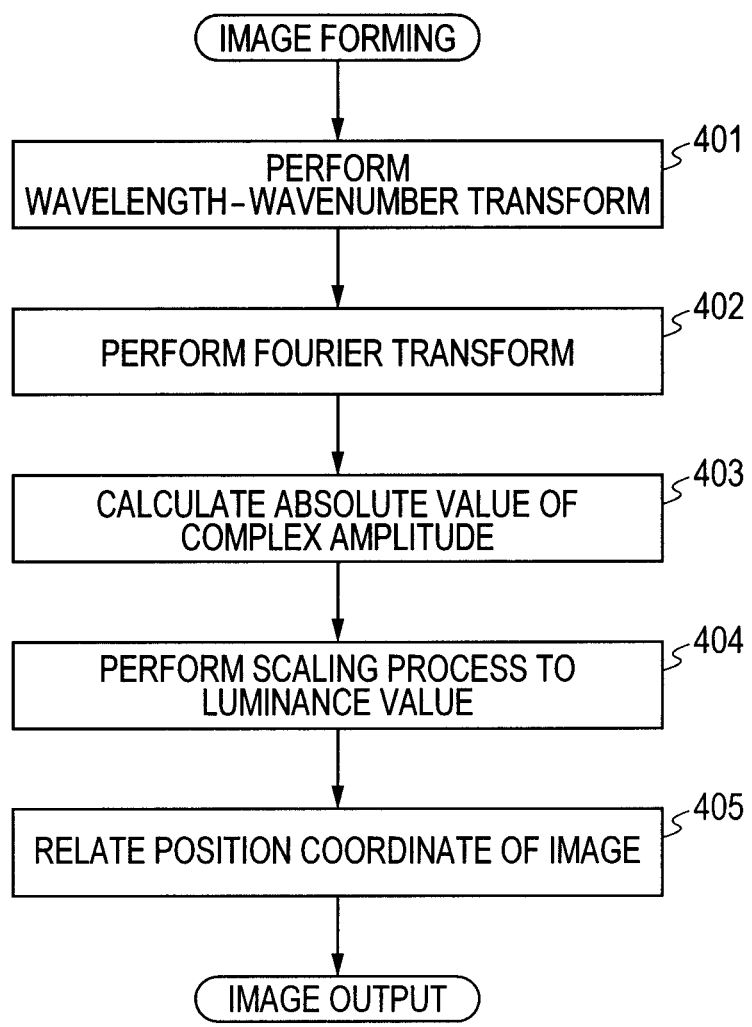

OPTICAL TOMOGRAPHIC IMAGING APPARATUS

TECHNICAL FIELD

The present invention relates to an imaging method and an imaging device for optical tomographic imaging, and more particularly, to an imaging method and an imaging device for optical tomographic imaging employing an optical coherence tomography used in, for example, ophthalmologic diagnosis and treatment.

BACKGROUND ART

In recent years, an optical coherence tomographic imaging method and an optical coherence tomographic imaging apparatus, to which a low coherence interferometer technology or a white light interferometer technology is applied, are in actual use. In particular, an optical tomographic imaging apparatus (optical interferometer apparatus) that performs optical coherence tomography (OCT) utilizing interference phenomenon of multi-wavelength light may obtain a tomogram of a sample with high resolution. Therefore, in the ophthalmological field, the optical tomographic imaging apparatus is becoming an indispensable apparatus for obtaining a tomogram of a fundus or a retina. In addition to the ophthalmological application, the optical tomographic imaging apparatus has also been used for tomographic observation of skin, tomography scan of a digestive and cardiovascular wall with an endoscope or a catheter constituted of the apparatus, or the like. Hereinafter, the optical tomographic imaging apparatus is referred to as an OCT apparatus.

In recent years, the Fourier domain optical coherence tomography (OCT) technology has developed, and, as a result, a period required for the imaging has significantly decreased compared with the conventional time domain optical coherence tomography (OCT). However, if an object such as a human eye is always moving, imaging conditions such as a position of focus and a position of a range of imaging change, resulting in problems such as a decrease in contrast and a frame out of the imaging range. It is thus necessary to obtain an image containing an area of interest as well as a peripheral area thereof for preventing the frame out and comparing the area of interest with the peripheral area thereof.

Japanese Patent Application Laid-Open No. 2009-042197 discloses a method of providing control for increasing an intensity of a signal for constructing an image if the intensity of the signal is less than a predetermined threshold value.

SUMMARY OF INVENTION

Technical Problem

However, with the method disclosed in Japanese Patent Application Laid-Open No. 2009-042197, there is a case in which the control of increasing the signal relating to an entire image including the peripheral area may conversely cause a decrease in signal intensity in the area of interest in the image. In addition to the case of using the intensity of the signal as the index, the same holds true for a case in which the SNR, the contrast, or the like is used as the index. It is therefore a problem to determine whether an area of interest in an OCT image has good image quality.

The present invention has been made in view of the above-mentioned problem, and therefore has an object to provide an optical tomographic imaging apparatus which enables an easy determination as to whether an obtained area of interest focused by a measuring person has good image quality.

Solution to Problem

In order to solve the above-mentioned problem, the present invention provides an optical tomographic imaging apparatus including: a light source for outputting a low coherence beam; a unit for splitting the low coherence beam into a measuring beam and a reference beam, and generating interference light by combining a return beam resulting from the measuring beam which has irradiated an object, and the reference beam which has passed through a reference optical path; a unit for detecting the interference light to generate a detection signal; a unit for forming an image of the object based on the detection signal; a unit for designating a specific area in the image; a unit for setting a calculation index and a determination reference range used for determining image quality of the specific area; and a unit for applying calculation processing to a luminance value of the specific area based on the calculation index, determining whether a calculated value obtained as a result of the calculation processing is within the determination reference range, and outputting a detection result.

According to the optical tomographic imaging apparatus of the present invention, it is possible to designate a specific area of interest in an OCT image, to designate a proper calculation index for determining the image quality of the area, and to determine whether the image quality of the area is good or not according to a calculated value obtained based on the calculation index. Therefore, it is possible to easily determine whether the obtained area of interest of a measuring person has good image quality.

Further features of the present invention will become apparent from the following description of exemplary embodiments with reference to the attached drawings.

BRIEF DESCRIPTION OF DRAWINGS

FIG. 4 illustrates an image forming step according to the embodiment.

DESCRIPTION OF EMBODIMENTS

An embodiment of the present invention is described referring to FIGS. 1 to 4. Though this embodiment employs the spectral domain OCT using a Michelson interferometer, the interferometer is not limited to the Michelson type.

Figure 1:
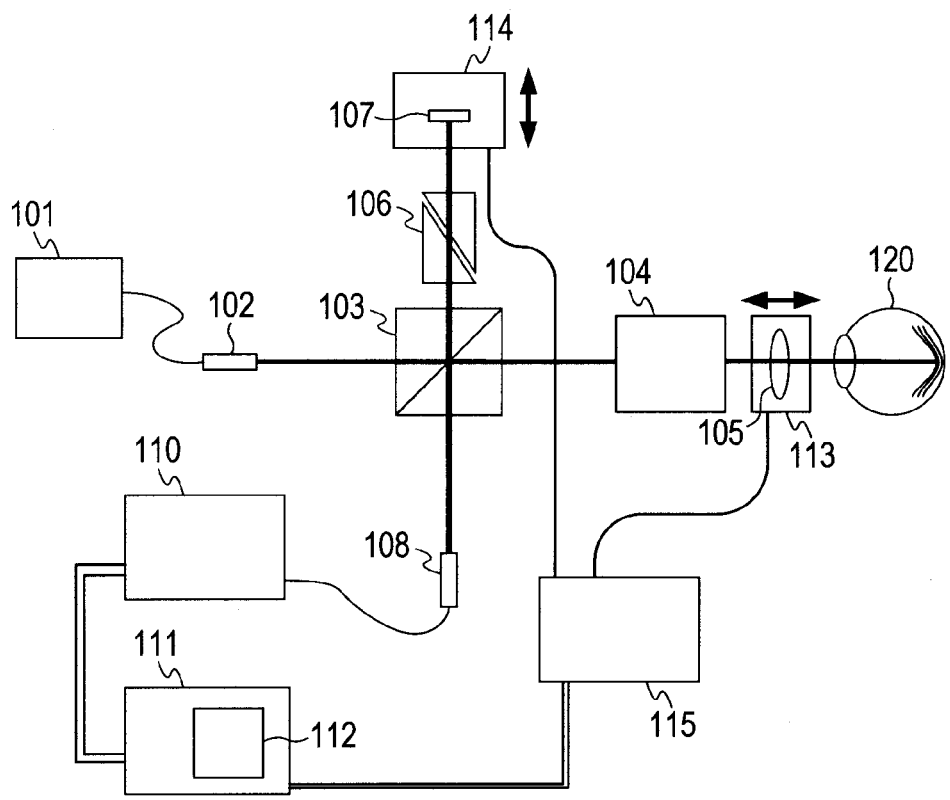
FIG. 1 illustrates a configuration of an OCT according to an embodiment.

FIG. 1 illustrates an overall configuration of an optical tomographic imaging apparatus of this embodiment.

A light beam emitted from a low coherence light source 101 passes through an optical fiber, and is collimated into a collimated light beam by a fiber collimator 102. This collimated light beam is split by a beam splitter 103 into a measuring beam and a reference beam.

The measuring beam irradiates an object 120 via a scanning optical system 104 constructed by two galvanometer mirrors and an ocular lens 105. The scanning optical system 104 can change a beam spot position on the object 120 twodimensionally. Moreover, the ocular lens 105 can change a focus position of the measuring beam by being moved in a direction of an optical axis using an electrically-operated stage 113. A return beam reflected or scattered by the object 120 travels along the previously-followed path in the opposite direction, and is returned via the ocular lens 105 and the scanning optical system 104 to the beam splitter 103.

On the other hand, the reference beam passes through dispersion compensation glass 106, is reflected by a reference mirror 107, travels along the previously-followed path again in the opposite direction, and is returned to the beam splitter 103. The reference mirror 107 is installed on an electrically-operated stage 114 which moves in a direction of an optical axis, thereby enabling adjustment of a reference optical path length. The dispersion compensation glass 106 is configured such that two dispersion prisms in a shape of a right triangle are arranged with oblique sides thereof opposed to each other, and can adjust the optical path length by displacing the positions thereof. The optical systems constructing the measuring optical path and the reference optical path are usually different, and thus have different chromatic dispersion amounts, which is not an optimal interference condition. The dispersion compensation glass 106 is thus inserted in the reference optical path to adjust the chromatic dispersion amount.

The return beam reflected or scattered by the object 120 and the reference beam returned by the reference mirror 107 are combined by the beam splitter 103 into interference light. The generated interference light is input by a fiber collimator 108 into an optical fiber, and is then input to a detection unit 110. The detection unit 110, which includes a diffraction grating for spectrally diffracting the interference light and a line sensor camera for detecting the spectrally diffracted interference light, converts the spectrally diffracted interference light into a digitized detection signal, and transmits the detection signal to a signal processing device 111. The signal processing device 111 includes image forming processing software for forming an image of the object 120 based on the detection signal, and a display device 112 for displaying the image of the object 120.

Figure 2:
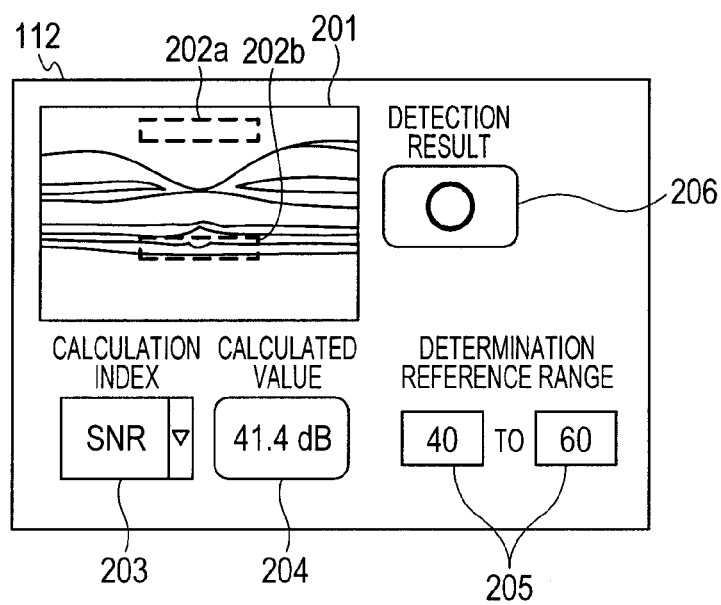
FIG. 2 illustrates a configuration of a display device according to the embodiment.

FIG. 2 illustrates a configuration of the display device 112. The display device 112 includes an image display portion 201, area setting portions 202a and 202b, a calculation index setting portion 203, a calculated value display portion 204, a determination reference range setting portion 205, and a detection result display portion 206. The image display portion 201 displays the image data processed by the signal processing device 111. The area setting portions 202a and 202b set areas subject to image evaluation in the displayed image. The calculation index setting portion 203 sets a calculation index for determining the quality of the displayed image. The calculated value display portion 204 displays a calculated value calculated in the areas set by the area setting portions 202a and 202b. The detection result display portion 206 displays a result of determination which indicates whether the calculated value is in a range set by the determination reference range setting portion 205.

Moreover, the signal processing device 111 may be configured to transmit the detection result to an electrically-operated stage control device 115 as illustrated in FIG. 1. This is described later.

Figure 3:
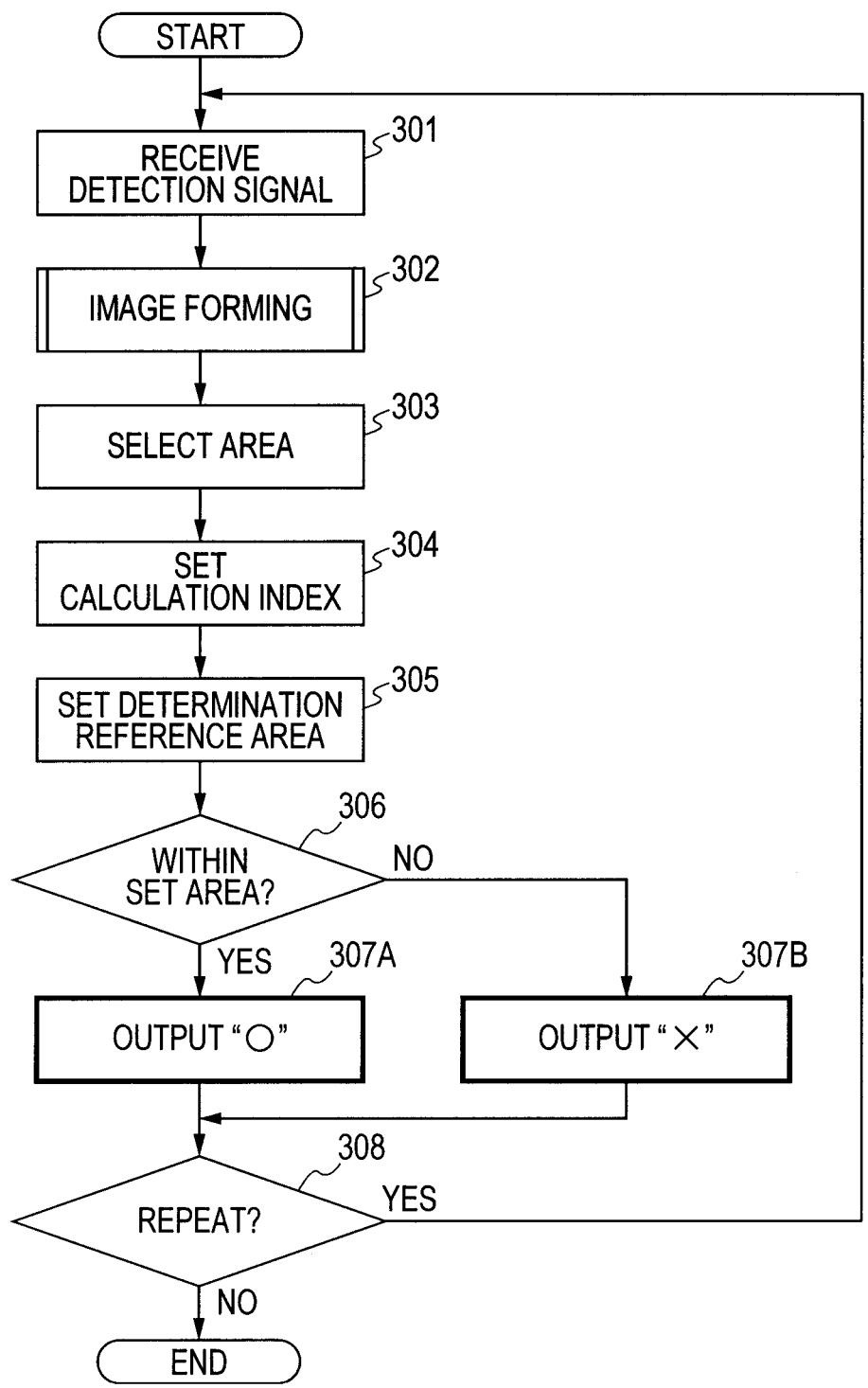
FIG. 3 illustrates processing steps performed by image forming software according to the embodiment.

FIG. 3 illustrates processing steps performed by the image forming processing software of the signal processing device 111. The image forming processing software first receives the detection signal transmitted from the detection unit 110, and transmits the detection signal to an image forming step (301). The detection signal is processed to form image data of the object 120 in the image forming step (302). The image forming processing software displays the image data on the image display portion 201, and receives the areas set by the area setting portions 202a and 202b (303). The image forming processing software then receives the calculation index set in the calculation index setting portion 203 (304). The image forming processing software further receives the determination reference range set in the determination reference range setting portion 205 (305). The image forming processing software extracts luminance values of the respective areas from the image data based on the above-mentioned information, and executes calculation processing on the luminance values based on the set calculation index. The image forming processing software compares the calculated value obtained as a result with the determination reference range, and determines whether the calculated value is within the determination reference range (306). If the calculated value is in the determination reference range, the image forming processing software outputs "○" (307A), and if the calculated value is out of the determination reference range, the image forming processing software outputs "x" (307B). If the operation continues, the image forming processing software returns to the start, and if the operation is finished, the image forming processing software finishes the processing (308).

FIG. 4 illustrates details of the image forming step (302) of FIG. 3. First, the detection signal transmitted by the detection unit 110 is a detection signal corresponding to wavelengths contained in the low coherence light source 101, and is transformed into a form corresponding to the wavenumber (reciprocal of the wavelength) before Fourier transform processing (401). This data is processed by means of the Fourier transform (402), and an absolute value of an output complex amplitude is calculated (403). The absolute value data is converted by means of common logarithm conversion into luminance values of 8-bit (256) gradation in order to display the absolute value data as an image (404). This luminance value data is related to position coordinates of the image (405), and is output as two-dimensional image data.

According to the configuration of this embodiment, it is possible to designate a specific area of interest in an OCT image, to designate a proper calculation index for determining the image quality of the area, and to determine whether the image quality of the area is good or not according to a calculated value obtained based on the calculation index, and it is thus possible to easily determine whether the obtained area of interest of a measuring person has good image quality.

Example 1

A specific example is described according to the embodiment illustrated in FIGS. 1 to 4.

A super luminescent diode (SLD) which has a center wavelength of 840 nm and a wavelength width of 45 nm is used as the low coherence light source 101. The object 120 is the human eye retina. The dispersion compensation glass 106 is made of BK7 glass, and is configured by using two dispersion prisms having a longer side of 20 mm and a shorter side of 15 mm. The longer sides are arranged so as to be parallel with the optical axis, and a standard refractive index liquid is applied to the oblique surfaces so that the oblique surfaces are adhered to each other. The thickness of the glass serving as the optical path can be changed in a range of approximately 20±10 mm by displacing the oblique surfaces.

The detection unit 110 is configured as described below. The line sensor camera has a pixel size of a 14-μm square, a pixel pitch of 14 μm, the number of pixels of 2048, and a line rate of up to 27 kHz. An optical system is arranged so that interference light input by the optical fiber is spectrally diffracted by a transmission-type diffraction grating of 1200 line/mm, and is converged on the line sensor camera. The interference light undergoes analog-digital conversion with a resolution of 12 bits in the line sensor camera, and is transmitted as the detection signal to the signal processing device 111.

A personal computer is used as the signal processing device. Moreover, a liquid crystal display of the personal computer is used as the display device 112.

According to this example, it is determined by focusing on the SNR (S/N ratio) of the pigmented layer of the retina whether the image quality of the image displayed on the image display portion 201 is good. The first area and the second area are designated by the area setting portions 202a and 202b, the calculation index is set to "SNR" in the calculation index setting portion 203, and the determination reference range is set to 40-60 [dB] in the determination reference range setting portion 205. The first area set by the area setting portion 202b is an area partially containing the pigmented layer of retina, and the SNR is determined while the second area set by the area setting portion 202a is considered as a background. The SNR is calculated according to the following equation from luminance values of pixels in each of the areas.

$$SNR = 20 \times \log\{(\text{maximum of luminance values in area } 202b)/(\text{standard deviation of luminance values in area } 202a)\}$$

The calculation result is displayed on the calculation result display portion 204. The calculation result is 41.4 dB in this example. This calculated value is within the determination reference range, and "0" is thus displayed on the detection result display portion 206.

The value of the SNR is directly displayed in the above-mentioned example. However, if values obtained by a scaling in which 40 dB is represented as 0 and 60 dB is represented as 100 are displayed considering the determination reference range of 40 to 60 dB, this may offer a more viewer-friendly display. Moreover, though the detection result is represented by "0" or "x", any one of brightness of light, color, sign, sound, and mechanical motion may be used as long as the representation enables a clear distinction as to whether the SNR is within the determination reference range or out of the determination reference range.

According to this example, whether an area of interest is clearly imaged can be easily determined by designating the area of interest in the obtained OCT image, and employing the SNR with respect to the background as the calculation index.

According to this example, though the example of the bulk optical system in which the beam splitter 103 is used is described, the same effect is obtained by constructing an optical fiber system using a fiber coupler. Moreover, though the signal processing by means of the spectral domain OCT is described in this example, the swept source OCT and the time domain OCT can provide the same effect.

Example 2

Figure 5A:
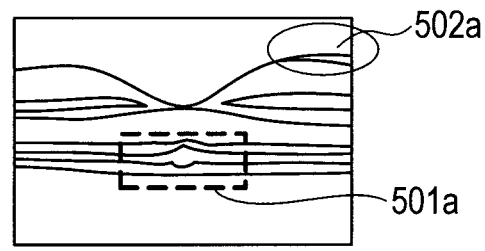
FIGS. 5A, 5B and 5C illustrate areas designation according to Example 2.
Figure 5B:
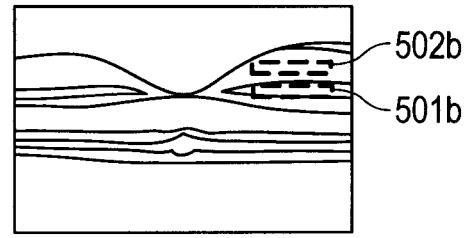
Figure 5C:
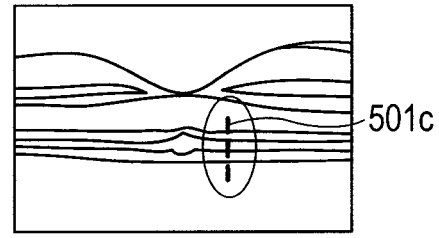

This example describes a case in which the calculation index is not SNR and the area designation is different referring to FIGS. 5A to 5C.

FIG. 5A illustrates a case in which an area 501a near the neuroepithelial layer of retina directly below the central fovea is designated. According to the spectral domain OCT, the signal intensity increases as the position becomes closer to the reference mirror, and the signal intensity thus tends to increase at a neighborhood 502a of the nerve fiber layer. Thus, whether the luminance value in the area 501a is good or not can be determined by designating the area 501a, and setting the calculation index to "Maximum value". In other words, it is possible to arbitrarily set an area of interest and to easily determine whether the luminance value is high or not.

FIG. 5B illustrates a case in which a neighborhood 501b of the internal granular layer and a neighborhood 502b of a layer next thereto are designated. In this case, it is possible to determine whether the neighborhood of the internal granular layer is separated from its peripheral portion, and is thus clearly imaged by setting the calculation index to "Contrast". An expression for "Contrast" is usually represented by:

$$|A1-A2|/(A1+A2)$$

where A1 denotes the average of luminance values in the area 501b, and A2 denotes the average of luminance values in the area 502b.

It should be noted that another definition expression:

$$|A1-A2|/\sqrt{(\delta1^2-\delta2^2)}$$

where $\delta1$ denotes the standard deviation of luminance values in the area 501b, and $\delta2$ denotes the standard deviation of luminance values in the area 502b, or even a simpler expression:

$$A1/A2$$

may be used. This method enables the determination whether areas of interest are imaged so as to be clearly distinguished from each other.

FIG. 5C illustrates a case in which an area 501c in a form of a straight line vertically crossing a neighborhood of the neuroepithelial layer is designated. In this case, it is possible to determine whether a resolution clearly resolves each of layers near the neuroepithelial layer by setting the calculation index to "SMF (sharpness metric function)". The number of pixels N having a luminance value exceeding a predetermined threshold value (such as 200) in this area 501c is 10, and the total number of pixels M in the area 501c is 41. The SMF can thus be calculated as:

$$SMF = N/M = 0.244$$

Moreover, the SMF may be simply N or 1/N.

The resolution of the OCT image varies depending on a spectral shape of the light source, polarized states of the measuring beam and the reference beam, and a degree of the dispersion compensation. This method enables an easy determination of the resolution of an area of interest.

Examples of calculation of the calculation indices other than the SNR are described in this example, the same effect as in Example 1 is provided if those values are scaled and then displayed.

Example 3

This example describes an example of designating an area by a name of a specific portion.

Though the examples in which the designation is made by a position coordinate in the image display portion 201 are described in the preceding section, there are cases in which an area is designated more conveniently by a name of a specific portion.

Figure 6:
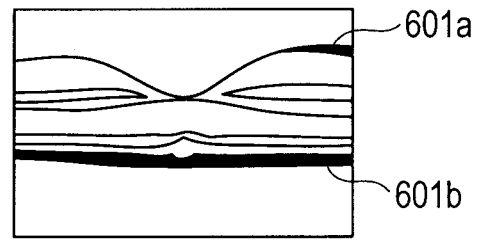
FIG. 6 illustrates area designation according to Example 3.

FIG. 6 illustrates a case in which an area is designated by "Nerve fiber layer" (601a), and a case in which an area is designated by "Pigmented layer" (601b). When a lesion is diagnosed using OCT images, a change in a specific portion is often focused upon usually, and the specific portion can be easily designated by the name rather than the position coordinate.

Each of layers can be discriminated in advance by applying processing of calculating boundaries of each of the layers from image data (segmentation). When the object 120 is the human eye retina, options such as "Nerve fiber layer", "External granular layer", "Internal granular layer", and "Nerve fiber layer" are provided for selection, and processing of storing a table, in which these options are respectively related to segmentation results, in a storage area of the personal computer is carried out. When a specific portion is selected, the area can be designated by referring to the table.

This method enables an easy selection of an area of interest of a person carrying out imaging.

Example 4

This example describes a case in which a device is controlled by an output of the detection result.

The detection result is only displayed on the detection result display portion 206 in the above-mentioned examples. Control of automatically obtaining and storing image data only if the image quality of an area of interest is good can be easily provided by using the detection result and the calculated value of the calculation index.

The detection result is transmitted from the signal processing device 111 to the electrically-operated stage control device 115 as illustrated in FIG. 1. The electrically-operated stage control device 115 operates the electrically-operated stages 113 and 114 according to the detection result.

An area is designated as "Nerve fiber layer" (601a) as illustrated in FIG. 6, and the calculation index is set to "Maximum value", and the determination reference range is set to 200 to 255. The electrically-operated stage control device 115 takes images by controlling the electrically-operated stage 113 while moving the electrically-operated stage 113 within a range of from −5 mm to +5 mm by a step of 0.2 mm with the initial position set to 0 mm. The image data obtained in each step on this occasion is determined according to the steps in FIG. 3, and the detection result and the image data related to each other are stored in the storage area of the signal processing device (personal computer) 111. Clear images of the "Nerve fiber layer", which is of interest, are obtained by selecting only image data whose detection result is "○" after the entire imaging is finished.

Though the method of storing all the image data and then selecting some of the image data is described in the above-mentioned example, the imaging may be finished when an image whose detection result is "○" is obtained. Moreover, only the detection result in each step of the electrically-operated stage 113 may be stored first, and the image is then taken by moving again the electrically-operated stage 113 to a position which gives the detection result "○".

Similarly, a method of controlling the electrically-operated stage 114 for the reference mirror 107 may be used. If electrically-operated stage 114 moves the reference mirror 107, the coherence gate, which means the axial range of imaging with the OCT measurement light, will be changed. When the coherence gate is proper for imaging the target layer the detection result display portion 206 displays the result "○", otherwise the result "x". Moreover, the same effects can be provided by controlling the amount of light, the spectral shape, and the polarization state of the SLD light source used as the low coherence light source 101, and the incident position of the measuring beam provided by the scanning optical system 104, which are not illustrated herein.

Example 5

This example describes a case in which the calculation index and the determination reference range are automatically selected corresponding to one of the designated area and the calculation index. In above mentioned examples, designation of the area in the step S303, set of the calculation index in the step S304, and set of the determination reference range in the step S305 are performed independently, as shown in the FIG. 3. In this example, the image forming processing software, is set so that the calculation index setting portion 203 sets the calculation index to "SNR" and the determination reference range setting portion 205 sets the determination reference range 40 db-60 db, corresponding to the designation of area by both the area setting portion 202a and 202b. This image forming processing software enables to reduce the number of mistakes that the user inputs wrong parameters into the system and improves the quality of image obtained under the control described in this example. Alternatively, it is also effective that a specific area or region of the subject eye are associated with a specific calculation index and a specific determination reference range, and the specific calculation index and the determination reference range are set in response to the designation of the specific area or region of the subject eye. And it is also effective that the determination reference range setting portion 205 sets a predetermined range in response to set of calculation index by the calculation index setting portion 203 to a specific index, associated with the predetermined range.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefits of Japanese Patent Applications No. 2010-070029, filed Mar. 25, 2010, and No. 2011-058979, filed Mar. 17, 2011 which are hereby incorporated by references herein in those entireties.

The invention claimed is:

1. An optical tomographic imaging apparatus comprising:
   a processor and a memory, cooperating to function as units comprising:
   (a) an image forming unit configured to form a tomographic image of an object based on an interference light generated by a measuring light which has passed through the object and a reference light which has passed through a reference optical path;

(b) an image display unit configured to display the tomographic image on a display device;

(c) an area setting unit configured to set, based on a user's operation, first and second partial areas within the tomographic image displayed on the display device;

(d) an image quality obtaining unit configured to obtain an image quality of an image of the second partial area as an image quality of the tomographic image, based on first values in the first partial area and second values in the second partial area, the first values in the first partial area being used as a reference value for calculating the image quality of the image of the second partial area;

(e) a determination unit configured to determine whether a value indicating the image quality obtained by the image quality obtaining unit satisfies a specific determination reference;

(f) an output unit configured to display, on the display device, a result of a determination of the determination unit; and (g) a control unit configured to control at least one of an amount of the measuring light for the object, a spectral shape of the measuring light, a polarization state of the measuring light, an incident position of the measuring light, and an optical path of the reference light, in accordance with the result of the determination, wherein the image forming unit forms a new tomographic image based on the controlling by the control unit.

2. An optical tomographic imaging apparatus according to claim 1, wherein the output unit displays on the display device, together with the result of the determination, the value indicating the image quality.

3. An optical tomographic imaging apparatus according to claim 1, wherein the control unit is configured to control the amount of the measuring light for the object, in accordance with the result of the determination.

4. An optical tomographic imaging apparatus according to claim 3, wherein the memory stores the result of the determination and a controlled position of a reference object on the reference optical path, which is directed to the result of the determination, and wherein the control unit selects the image obtained at the controlled position satisfying the determination reference, and causes the memory to store the image obtained at the controlled position satisfying the determination reference.

5. An optical tomographic imaging apparatus according to claim 1, wherein the processor and the memory further cooperate to function as a setting unit configured to set a kind of the value indicating the image quality, and the specific determination reference, based on a user's operation.

6. An optical tomographic imaging apparatus according to claim 5, wherein the setting unit sets the kind of the value designating the image quality and the specific determination reference, in accordance with the first partial area and the second partial area which have been set by the area setting unit.

7. An optical tomographic imaging apparatus according to claim 5, wherein the setting unit sets an area within the tomographic image based on a name of a specific portion selected by a user, and wherein the setting unit sets the kind of the value indicating the image quality and the specific determination reference, in accordance with the name which has been selected by the user.

8. An optical tomographic imaging apparatus according to claim 5, wherein the setting unit sets the specific determination reference in accordance with the kind of the value indicating the image quality, which has been set by the setting unit.

9. An optical tomographic imaging apparatus according to claim 1, wherein the image quality obtaining unit obtains the image quality based on one of (a) a ratio of standard deviation of luminance values in the first partial area and a maximum of luminance values in the second partial area, and (b) a value calculated based on the ratio.

10. An optical tomographic imaging apparatus according to claim 1, wherein the image quality obtaining unit obtains the image quality and uses, as the value indicating the image quality, any one of (a) calculated values calculated by any one of equations of:

$$A1/A2;$$

$$|A1-A2|/(A1+A2); \text{ and}$$

$$|A1-A2|/\sqrt{\delta1^2-\delta2^2},$$

where $A1$ and $\delta1$ respectively denote an average value and a standard deviation of luminance values in the first partial area, and $A2$ and $\delta2$ respectively denote an average value and a standard deviation of luminance values in the second partial area, and (b) a value calculated based on the calculated value.

11. An optical tomographic imaging apparatus according to claim 10, wherein the equation $A1/A2$ is used.

12. An optical tomographic imaging apparatus according to claim 10, wherein the equation $|A1-A2|/(A1+A2)$ is used.

13. An optical tomographic imaging apparatus according to claim 10, wherein the equation $|A1-A2|/\sqrt{\delta1^2-\delta2^2}$ is used.

14. An optical tomographic imaging apparatus according to claim 1, wherein the processor and the memory further cooperate to function as an image selection unit configured to select the tomographic image based on the result of the determination of the determination unit.

15. An optical tomographic imaging apparatus according to claim 1, further comprising a light source.

16. An optical tomographic imaging apparatus according to claim 1, wherein after the image forming unit forms the new tomographic image, the operations of (b) through (g) are performed using the new tomographic image.

17. An optical tomographic imaging method using an optical tomographic imaging apparatus, which apparatus includes a processor coupled to a memory, the method comprising the steps of:

(a) forming a tomographic image of an object based on an interference light generated by a measuring light which has passed through the object and a reference light which has passed through a reference optical path;

(b) displaying the tomographic image on a display device;

(c) setting, based on a user's operation, first and second partial areas within the tomographic image displayed on the display device;

(d) obtaining an image quality of an image of the second partial area as an image quality of the tomographic image, based on first values in the first partial area and second values in the second partial area, the first values in the first partial area being used as a reference value for calculating the image quality of the image of the second partial area;

(e) determining whether a value indicating the image quality obtained in the image quality obtaining step satisfies a specific determination reference;

(f) displaying, on the display device, a result of a determination in the determination step; and (g) controlling at least one of an amount of the measuring light for the object, a spectral shape of the measuring light, a polarization state of the measuring light, an incident position of the measuring light, and an optical path of the reference light, in accordance with the result of the determination, wherein a new tomographic image is formed based on the controlling by the controlling step.

18. A non-transitory medium having a program recorded thereon, for controlling a computer to execute the optical tomographic imaging method according to claim 17.

19. An optical tomographic imaging method according to claim 17, wherein after the new tomographic image is formed, the operations of (b) through (g) are performed using the new tomographic image.

* * * * *